United States Patent
Lane et al.

(10) Patent No.: US 8,136,985 B2
(45) Date of Patent: Mar. 20, 2012

(54) IR THERMOMETER THERMAL ISOLATION TIP ASSEMBLY

(75) Inventors: John A. Lane, Weedsport, NY (US); David E. Quinn, Auburn, NY (US); Scott A. Martin, Warners, NY (US); Ray D. Stone, Camillus, NY (US); Matthew D. Mullin, Memphis, NY (US); Craig M. Meyerson, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 323 days.

(21) Appl. No.: 12/435,731

(22) Filed: May 5, 2009

(65) Prior Publication Data

US 2010/0284436 A1 Nov. 11, 2010

(51) Int. Cl.
 *G01K 1/08* (2006.01)
 *G01J 5/04* (2006.01)
 *A61B 5/01* (2006.01)

(52) U.S. Cl. ........ 374/121; 374/208; 374/209; 374/158; 600/474

(58) Field of Classification Search .......... 374/120, 374/121, 126, 131, 158, 208, 209
 See application file for complete search history.

(56) References Cited

U.S. PATENT DOCUMENTS

| | | | |
|---|---|---|---|
| 4,191,197 A * | 3/1980 | Benzinger | 600/549 |
| 4,993,419 A | 2/1991 | Pompei | |
| 5,018,872 A * | 5/1991 | Suszynski et al. | 374/133 |
| 5,188,459 A * | 2/1993 | Mino et al. | 374/158 |
| RE034,507 E | 1/1994 | Egawa | |
| 5,293,877 A | 3/1994 | O'Hara | |
| 5,325,863 A | 7/1994 | Pompei | |
| 5,368,038 A | 11/1994 | Fraden | |
| 5,645,350 A | 7/1997 | Jang | |
| 5,820,264 A | 10/1998 | Tsao | |
| 5,857,775 A | 1/1999 | Vodzak | |
| 6,102,564 A | 8/2000 | Egawa | |
| 6,109,782 A | 8/2000 | Fukura | |
| 6,152,595 A | 11/2000 | Beerwerth | |
| 6,156,148 A | 12/2000 | Beerwerth | |
| 6,179,785 B1 | 1/2001 | Martinosky | |
| 6,186,956 B1 | 2/2001 | McNamee | |
| 6,332,090 B1 | 12/2001 | DeFrank | |
| 6,416,602 B1 | 7/2002 | Firatli | |
| 6,572,264 B1 | 6/2003 | Egawa | |
| 6,631,287 B2 | 10/2003 | Newman | |
| 6,634,787 B1 | 10/2003 | Beerwerth | |
| 6,694,174 B2 | 2/2004 | Kraus | |
| 6,695,474 B2 | 2/2004 | Beerwerth | |

(Continued)

OTHER PUBLICATIONS

European Patent Office; International Search Report from PCT/US2010/033080; Oct. 14, 2010.

*Primary Examiner* — Amy Cohen Johnson

(57) ABSTRACT

An IR tip assembly includes a shroud having at least one feature that permits releasable attachment of a disposable cover fitted to a shroud. When the disposable cover is fitted to the shroud, at least one air gap is defined between the shroud and the disposable cover. An IR sensor disposed within the IR tip assembly is mechanically and thermally coupled to a heat sink. The at least one defined air gap creates a thermal isolation between the disposable cover and the disposed IR sensor. There can also be airflow through the at least one air gap. Apparatus and methods to create the airflow are described.

30 Claims, 14 Drawing Sheets

U.S. PATENT DOCUMENTS

| | | |
|---|---|---|
| 6,749,334 B2 | 6/2004 | Lin |
| 6,821,016 B2 | 11/2004 | Sato |
| 6,991,368 B2 | 1/2006 | Gerlitz |
| 7,048,437 B2 | 5/2006 | Bellifernine |
| 7,121,720 B2 | 10/2006 | Beerwerth |
| 7,237,949 B2 | 7/2007 | Lantz |
| 7,275,867 B2 | 10/2007 | Lee |
| 7,329,044 B2 | 2/2008 | Sato |
| 7,354,194 B2 * | 4/2008 | Walker et al. ............. 374/158 |
| 7,665,892 B2 * | 2/2010 | Hsieh ........................ 374/121 |
| 2002/0163953 A1 | 11/2002 | Yu |
| 2002/0176479 A1 | 11/2002 | Hur |
| 2002/0186745 A1 | 12/2002 | Pompei |
| 2002/0191670 A1 | 12/2002 | Huang |
| 2003/0016728 A1 | 1/2003 | Gerlitz |
| 2003/0067957 A1 | 4/2003 | Ko |
| 2004/0013162 A1 | 1/2004 | Beerwerth |
| 2004/0028116 A1 | 2/2004 | Lin |
| 2004/0228386 A1 | 11/2004 | Tabata |
| 2005/0002437 A1 | 1/2005 | Fraden |
| 2006/0050769 A1 | 3/2006 | Lee |
| 2006/0062274 A1 | 3/2006 | Pompei |
| 2006/0153278 A1 | 7/2006 | Chen |
| 2006/0198424 A1 | 9/2006 | Chen |
| 2006/0215728 A1 | 9/2006 | Jang |
| 2006/0239329 A1 | 10/2006 | Tanaka |
| 2006/0239332 A1 | 10/2006 | Harr |
| 2007/0127545 A1 | 6/2007 | Lee |
| 2007/0206657 A1 | 9/2007 | Lin |
| 2007/0206675 A1 | 9/2007 | Tanaka |
| 2007/0211783 A1 | 9/2007 | Huang |

* cited by examiner

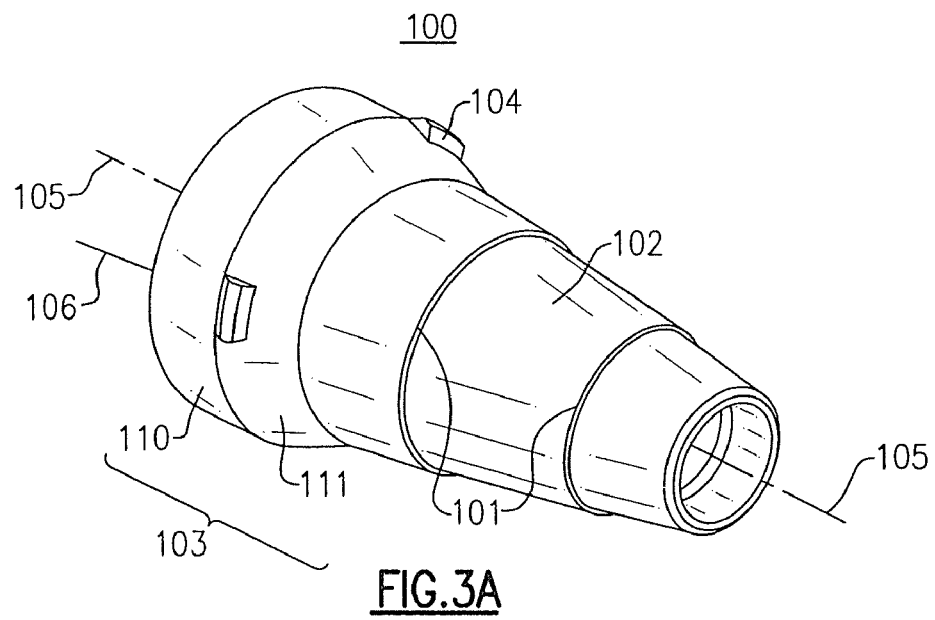
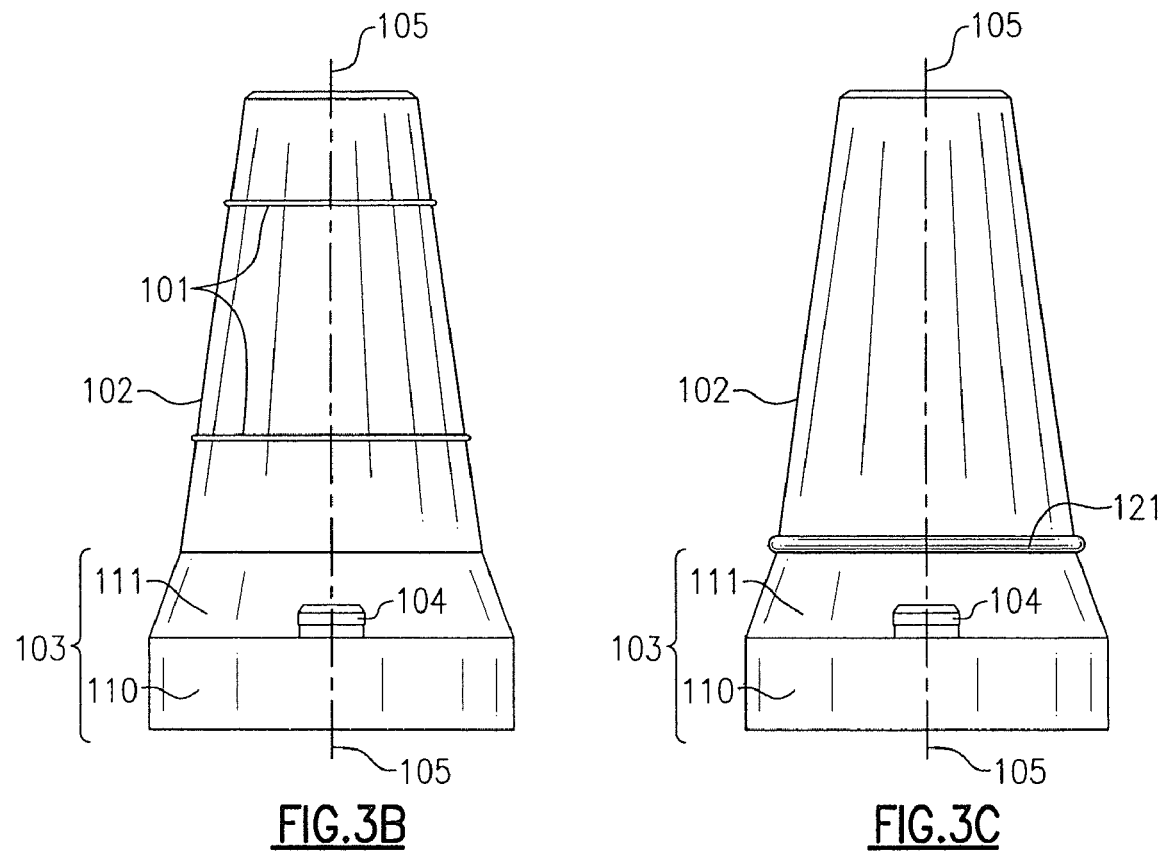

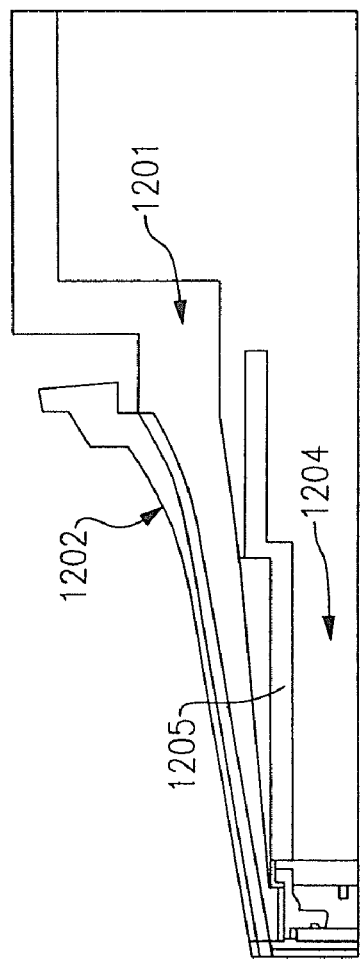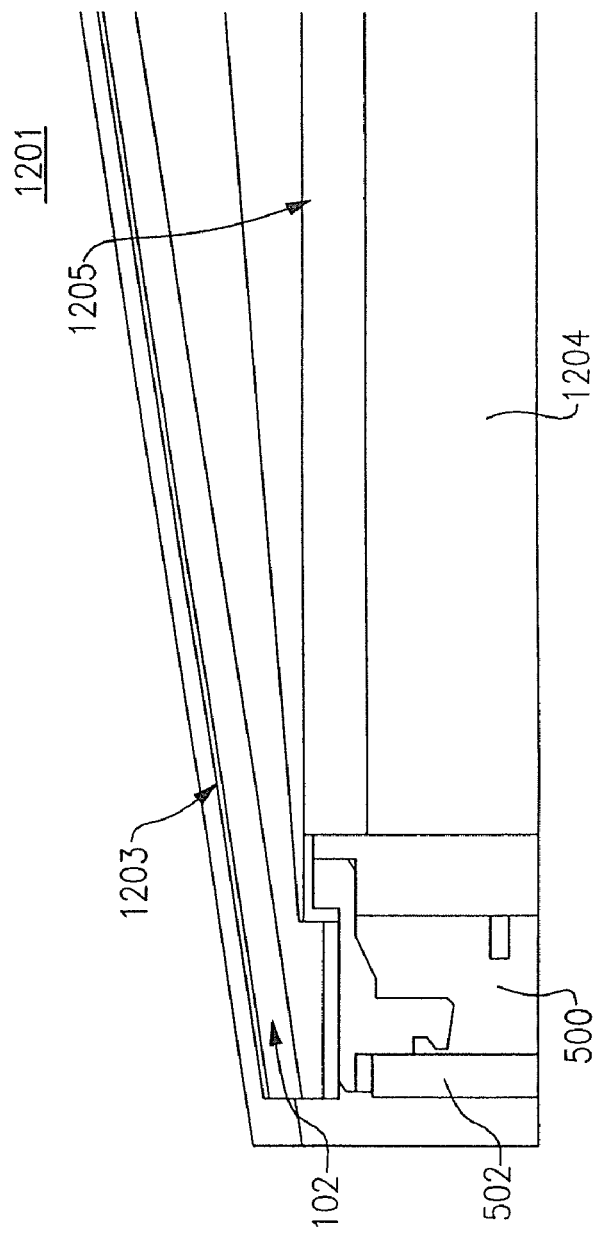

IR THERMOMETER THERMAL ISOLATION TIP ASSEMBLY

FIELD OF THE INVENTION

This invention relates generally to a tip assembly for an IR thermometer and more specifically to an IR tip assembly having improved thermal isolation.

BACKGROUND OF THE INVENTION

Infrared (IR) thermometers, such as IR ear thermometers, are in wide use today. IR thermometers employ an IR sensor to receive and measure IR radiation emanating from a surface. In the case of the IR ear thermometer, the IR sensor detects IR radiation that emanates from the surface of the tympanic membrane. One of the problems encountered in IR thermometry is that the electrical output of most IR sensors is a function of both the IR radiation received through the optical sensor window of the IR sensor, as well as the temperature of the sensor case or housing, typically a metal can.

Some IR thermometer instruments measure the temperature of the IR sensor housing in order to make a correction to the sensor electrical output signal. However, even with temperature sensing of the IR sensor can, there can be measurement errors related to changing temperature gradients across the instrument, particularly across elements of the IR thermometer in and near the optical path to the IR sensor and in the vicinity of the IR sensor housing (the "IR tip assembly"). Several approaches to thermally isolate sensitive areas of the IR thermometer from ambient heat sources have been used, such as the use of thermally insulating sections or the addition of diversionary thermally conductive paths to channel undesired heat flow away from the IR sensor.

Another problem, particularly in patient contact applications such as with IR ear thermometers, is to prevent patient cross-contamination. Generally, a thin plastic disposable cover such as a speculum is placed over an IR tip assembly to minimize the risk of patient cross-contamination as well as to keep the IR tip assembly as free as possible from bodily materials such as cerumen.

Also, regarding the disposable cover, there is an undesirable path for stray conduction of heat energy from the walls of the auditory canal through the disposable plastic cover to the IR tip assembly. There has been some effort to provide disposable covers having thermally insulating materials, however, use of such materials increase the cost of the disposable cover.

What is needed, therefore, is an IR tip assembly that can use a low cost disposable cover without introducing significant measurement error due to undesired heat conduction through the cover.

SUMMARY OF THE INVENTION

According to one aspect an IR tip assembly includes an IR sensor having an IR sensor base and an IR sensor side surface. The IR sensor is disposed within the IR tip assembly. A heat sink is mechanically and thermally coupled to the IR sensor base. A shroud overlays the IR sensor and the heat sink. The shroud includes at least one cover attachment feature. The shroud is thermally isolated from the IR sensor side surface. The shroud is also configured to releasably accept a disposable cover. When the disposable cover is attached to the shroud, at least one air gap is defined between the shroud and the disposable cover.

In one embodiment, a base of the shroud includes an annular protruding section. The protruding section is adapted to releasably accept a base of the disposable cover.

In another embodiment, the at least one feature includes at least one raised contact element on an exterior of the shroud.

In yet another embodiment, the at least one raised contact element includes a nub or protrusion.

In yet another embodiment, the at least one raised contact element includes at least one rib.

In yet another embodiment, the at least one rib includes at least a selected one of a linear rib, a spiral rib, and a circular rib.

In yet another embodiment, a plurality of ribs are disposed on the exterior of the shroud in a substantially linear pattern, each rib running between a proximal end and a distal end of the shroud.

In yet another embodiment, a plurality of ribs are disposed on the exterior of the shroud in a substantially linear pattern, each rib having a length dimension that is less than the length from the proximal end to the distal end.

In yet another embodiment, a plurality of rib segments distributed along the exterior of the shroud.

In yet another embodiment, the tip assembly includes a gap of at least 0.002" between a portion of an inner surface of the disposable cover and the exterior of the shroud when the cover is attached.

In yet another embodiment, the shroud is a part of the heat sink.

In yet another embodiment, the heat sink is defined by a material having a high thermal conductivity, such as a metal, for example, in one version aluminum.

The heat sink can be selected from the group of metals consisting of steel, brass, copper, copper alloy, aluminum, and aluminum alloy.

In yet another embodiment, the tip assembly further includes at least one air gap between the IR sensor side surface and the shroud.

In yet another embodiment, the tip assembly further comprises a plurality of insulative members between the IR sensor side surface and the shroud.

In yet another embodiment, the tip assembly is threadedly attached to an IR thermometer body.

In yet another embodiment, an additional layer of insulative material overlays the shroud and the at least one cover attachment feature is disposed at least in part on an outer surface of the additional layer of insulative material.

In yet another embodiment, an IR thermometer includes an IR tip assembly according as described above. A microcomputer-based circuit is electrically coupled to the IR sensor. The microcomputer-based circuit is configured to accept an electrical signal from the IR sensor and to generate a mammalian body temperature based at least in part on the electrical signal from the IR sensor.

In yet another embodiment, the IR thermometer includes a micro fan blower.

In yet another embodiment, the IR thermometer includes an IR thermometer body having at least one squeezable air chamber.

In yet another embodiment, the IR thermometer includes a pneumatically attached air bulb.

In yet another embodiment, the IR thermometer includes an air piston mechanically coupled to a temperature measure trigger.

In another aspect, a method to enhance the thermal isolation of an IR thermometer IR sensor during a temperature measurement includes the steps of: providing an IR thermometer having at least one air gap disposed between an IR sensor and a disposable cover; and causing an airflow through the at least one air gap during a temperature measurement to reduce a temperature change of the IR sensor caused by undesired heat flow across the disposable cover.

In one embodiment, the step of causing airflow includes causing airflow through the at least one air gap by squeezing an air chamber on an IR thermometer body.

In another embodiment, the step of causing an airflow includes causing an airflow through the at least one air gap by squeezing an air bulb pneumatically coupled to the air gap.

In yet another embodiment, the step of causing an airflow includes causing an airflow through the at least one air gap by air pressure from a micro blower.

In yet another embodiment, the step of causing an airflow includes causing an airflow through the at least one air gap by air pressure from a pneumatic piston that moves when an IR temperature measurement trigger is pulled.

BRIEF DESCRIPTION OF THE DRAWINGS

For a further understanding of these and objects of the invention, reference will be made to the following Detailed Description, which is to be read in connection with the accompanying drawings, where:

FIG. 3A shows a perspective view of an exemplary embodiment of a thermally isolating IR tip assembly having circular ribs;

FIG. 3B shows a side view of the exemplary tip of FIG. 3A;

FIG. 3C shows one embodiment of a tip assembly in which a disposable cover (not shown) can releasably attach near a base of the tip assembly;

FIG. 5A is a block diagram illustrating details of an embodiment of the IR ear thermometer illustrated in FIG. 5;

FIG. 5B is a block diagram illustrating details of another embodiment of the IR ear thermometer illustrated in FIG. 5;

FIG. 5C is a block diagram illustrating details of yet another embodiment of the IR ear thermometer illustrated in FIG. 5;

FIG. 5D is a block diagram illustrating details of another embodiment of the IR ear thermometer illustrated in FIG. 5;

FIG. 11A shows an exemplary cut away line drawing of an axisymmetric thermal model of one half IR tip assembly with a disposable cover;

FIG. 11B shows an exploded view of the IR tip assembly of FIG. 11A; and

The drawings are not necessarily to scale, emphasis instead generally being placed upon illustrating the principles of the invention. In the drawings, like numerals are used to indicate like parts throughout the various views.

DETAILED DESCRIPTION

Figure 1A:
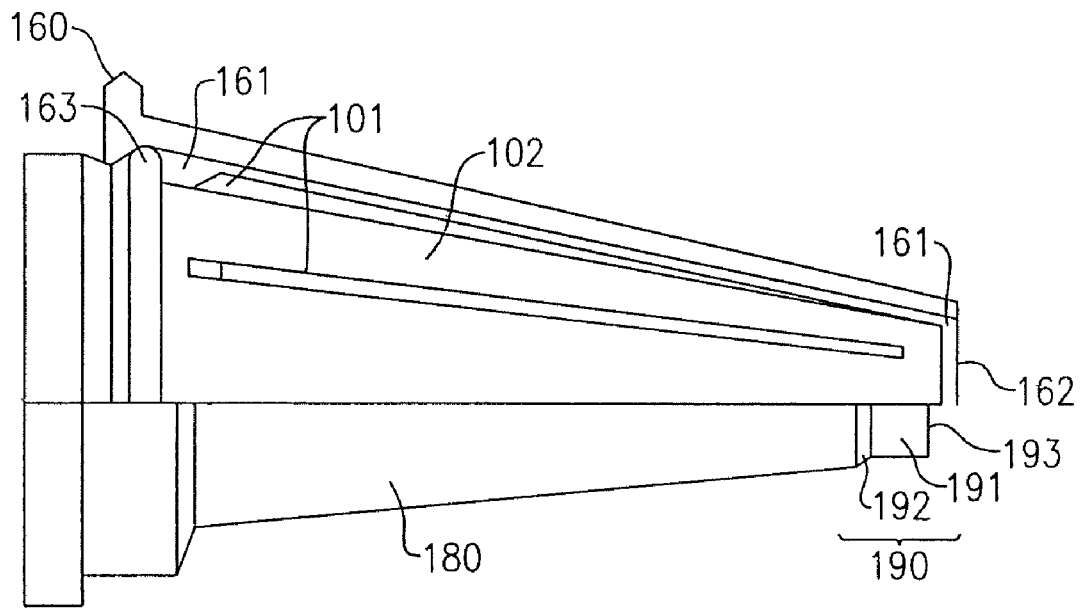
FIG. 1A shows a nested section view of another exemplary embodiment of a thermally isolating IR tip assembly with ribs.

For purposes of background, there are at least three (3) thermal paths of undesirable heat flow from the outside environment into an IR tip assembly of an IR thermometer. As discussed above, one path is directly from an outer surface of a disposable cover, into the tip section of the IR tip assembly. Another path is from the tip section of the IR tip assembly into an internal heat sink. Also, there can be an undesirable heat flow from the tip section directly to the IR sensor. An IR tip assembly, or thermally isolating IR tip assembly as described below, includes features to reduce undesired heat flow, including a new approach to thermally isolate a disposable cover from the tip assembly.

In the prior art, there has been an effort to reduce undesired heat flow that flows through a cover attached to an IR tip assembly. One approach has been to make disposable covers from one or more thermally insulating materials. A nearly opposite approach, described herein and using a relatively thin and thus low cost disposable cover turns out to provide a more ideal thermal isolation solution. This new approach has been made possible by the surprising realization that a relatively small thermally isolating air gap (e.g. on the order of 2 mils (0.002″) or more) created between an IR tip section (typically a shroud in the case of an IR ear thermometer) and a thin disposable cover can provide adequate thermal isolation between the disposable cover and the tip section. Such thin disposable covers can be made available at low cost, thus further encouraging use of such covers in all settings to reduce the danger of cross-contamination through re-use.

In the description which follows, several approaches to provide a reasonably effective thermally isolating air gap are described. In general, a disposable cover attaching structure (an attaching feature) can be provided on an IR tip assembly for releasably attaching a disposable cover to the IR tip assembly. The disposable cover can be attached to the IR tip assembly so as to create one or more air gaps between an outer surface of the tip section of the IR tip assembly and an inner surface of the disposable cover. For example, in some embodiments, the tip section of an IR tip assembly can be configured with numerous varied structural features including one or more simple mechanical contact elements, such as contact points (e.g. "nubs") or raised contact surfaces to one or more ribs that can support a disposable cover above the surface of a tip section. In another embodiment described in more detail below, a disposable cover can have a base flange that attaches a shroud of a tip assembly. The disposable cover can be sized to leave an air gap between the cover and the tip section, except at the base flange which is used to lock the cover to the tip, such as by a snap action.

Also, in the prior art, the tip section of the IR tip assembly has been manufactured from a thermally insulating material, such as a plastic, or there has typically been added a thermally insulating shroud over a tip section. While the new structure can include a thermally insulating shroud, another surprising result of using one or more structures to support a disposable cover over a tip section, is that in some embodiments, the shroud need not be made of a thermally insulating material.

FIG. 1A shows a nested section view of one exemplary embodiment of a thermally isolating IR tip assembly. An IR sensor 190 is disposed within the IR tip assembly. The IR sensor 190 includes an IR sensor base 192, an IR side surface 191, and an IR sensor window 193. The IR sensor base 192 is mechanically and thermally affixed to a heat sink 180. While IR sensor base 192 is mechanically and thermally affixed to a heat sink 180, notice that IR side surface 191, typically of a cylindrical form, is thermally isolated from any nearby structure such as shroud 102. In some embodiments, IR side surface 191 is completely surrounded by air and contact-free with the exception of the contact points where the IR sensor base 192 is bonded to the heat sink. In other embodiments, as discussed below, there can be thermally insulative support structures (not shown In FIG. 1A) to optically align IR sensor 190 within the tip assembly. Where thermally insulative support structures are used, there are still typically one or more air gaps between the support structures to assist in thermally isolating IR side surface 191 from, for example, shroud 102.

A shroud 102 overlays heat sink 180. Shroud 102 includes a cover attachment feature, e.g. a circular protuberance 163, to releasably accept a disposable cover 160. Shroud 102 helps to re-direct heat flow away from the IR sensor 190. Shroud 102 sets up a series of thermal interfaces. The first interface is the air gap between the probe cover and the shroud. The second interface is where heat is channeled from shroud 102 to a mechanical and thermal connection with heat sink 180 (e.g. via a threaded connection) to heat sink 180. The third interface is the air gap between shroud 102 and IR sensor 190.

Figure 1B:
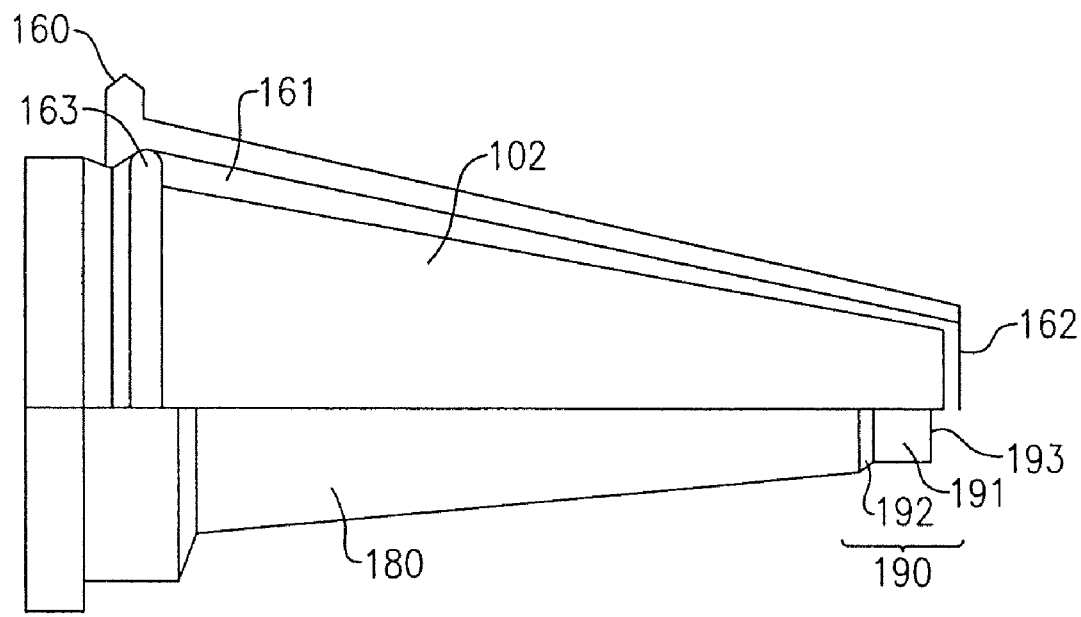
FIG. 1B shows a nested section view of one exemplary embodiment of a thermally isolating IR tip assembly.

Disposable cover 160 includes a substantially transparent IR window 162. In the embodiment of FIG. 1A, disposable cover is supported in part by ribs 101. An air gap 161 is defined between shroud 102 and disposable cover 160. FIG. 1B shows a nested section view of another exemplary embodiment of a thermally isolating IR tip assembly without ribs. In this "witches hat" embodiment of FIG. 1B, disposable cover 160 is fully supported by the cover attachment feature, such as circular protuberance 163.

Figure 1C:
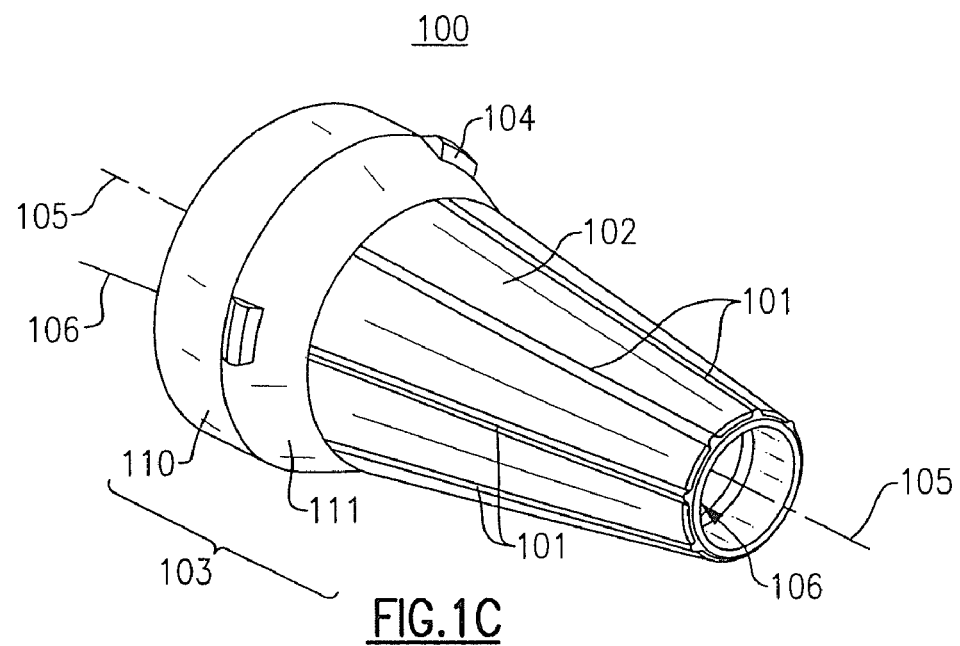
FIG. 1C shows a perspective view of an exemplary embodiment of a thermally isolating IR tip assembly.

Turning now in more detail to an exemplary thermal isolation structure to support a disposable cover, FIG. 1C shows a perspective view of a first exemplary embodiment of a thermally isolating IR tip assembly 100. The herein described IR tip assembly 100 includes a base section 103 proximal to a IR thermometer body (farthest from a patient's ear) and an inward tapering section 102 extending from base 103 to the distal end farthest from the IR thermometer body. In use, IR tip assembly 100 is typically covered by a "slide-on" disposable (speculum) cover (not shown in FIG. 1C). The shroud 102 and cover are typically small enough to be inserted a predetermined distance into the auditory canal of a patient's ear, but wherein this distance prevents damage to the patient. Shroud 102 includes a plurality of axially disposed ribs 101, which in the exemplary embodiment of FIG. 1C, are oriented generally in a direction from the proximal end of the shroud 102 to the distal end thereof. Exemplary alternative rib patterns are described in more detail below. In the exemplary embodiment of FIG. 1C, the ribs 101 are substantially aligned with guide line 106, running parallel to the surface of shroud 102.

Ribs 101 create channels there between, these channels creating an air gap that provides thermal isolation between the auditory canal of a patient's ear and IR tip assembly 100. Thus, undesirable heat flow from the auditory canal of a patient's ear to IR tip assembly 100 and the IR thermometer body (not shown in FIG. 1C) can be minimized. It was a surprising and unexpected result that ribs 101 of relatively small relief (height), of about 2 thousandths of inch or more in height, are still highly effective to reduce the undesirable heat flow from the disposable cover to the IR tip assembly, as described above. The air pockets formed between an attached disposable cover and IR tip assembly 100, and ribs 101 provide the thermal isolation. In some embodiments as described below, a flow of air through those pockets, either by convective means or forced airflow, can enhance the thermal isolation between a disposable cover (and its exterior sources or sinks of heat) and an IR tip assembly 100. As is described below in more detail, airflow under a disposable cover is most helpful for limiting heat flow during a relatively short time interval (e.g. at the beginning of an IR ear temperature measurement), while the heat sink captures and directs heat over a relatively longer time interval.

Figure 1D:
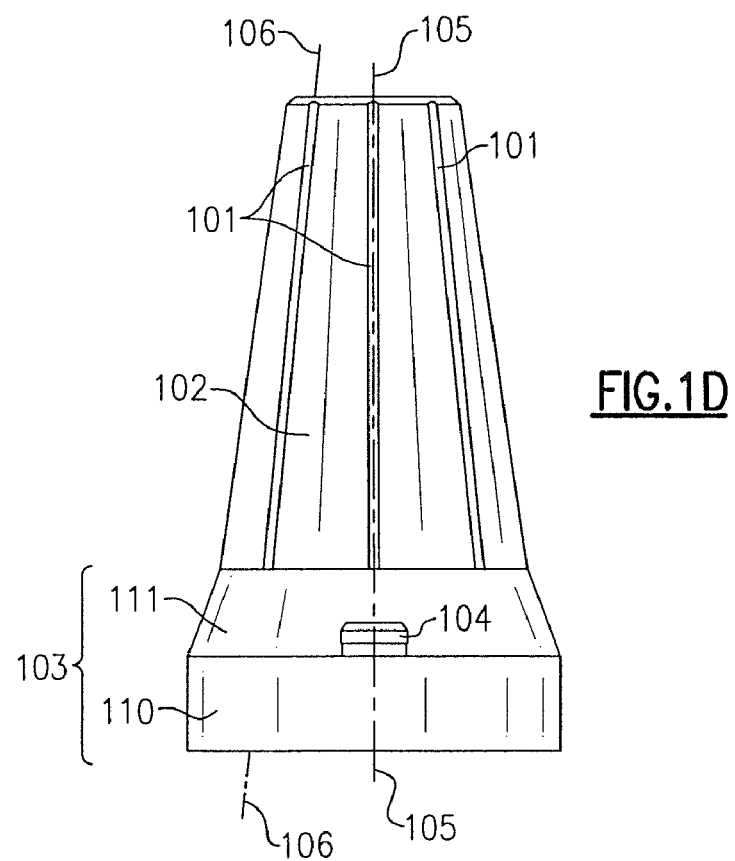
FIG. 1D shows a side view of the exemplary tip of FIG. 1C.

Continuing with the exemplary embodiment of FIG. 1C and FIG. 1D, the exact shape, or in some embodiments the presence of, base section 103 is unimportant to the operation of the tip as described herein. At the proximal end of IR tip assembly 100, there is a relatively non-tapering cylindrical section 110 followed by a transition at section 111 of the base section 103, that leads into a shroud 102. At least one fixed seating feature 104, and/or a disposable cover ejector mechanism (not shown in FIG. 1C) can provide mechanical or electromechanical ejection of a sanitary (disposable) cover after each use. These and other types of mechanical features on or near base section 103 can be used permit a disposable cover to remain engaged with the IR tip assembly 100 for the duration of a measurement. It is unimportant to the invention that a base section 103 includes two sections, as described herein, or that a base section be present at all. That is, the entirety of the IR tip assembly can be formed from frusto-conical (e.g. tapering) configuration.

Similarly, the exact shape of the shroud 102 is unimportant to the operation of the tip as described herein. Shroud 102 is shown as a frusto-conical section in FIG. 1C and FIG. 1D. However, while guide line 106 is shown in FIG. 1C as a substantially straight line, there is no need for the shroud to strictly follow a conic section. For example, the sides of shroud 102 can be substantially of a linear taper, such as a conic section, or can also include non-linear tapers, such as curved concave or convex forms (e.g. a taper that varies from the proximal to distal end of IR tip assembly 100).

Figure 2A:
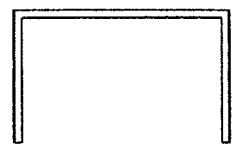
FIG. 2A shows a cross section of a rectangular rib.
Figure 2B:
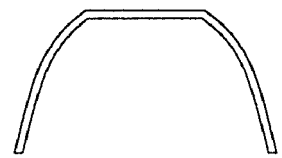
FIG. 2B, shows a cross section of a rectangular shape with rounded sides.
Figure 2C:
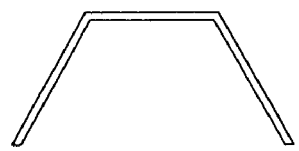
FIG. 2C shows a cross section of a rectangular shape with slanted or angled sides.
Figure 2D:
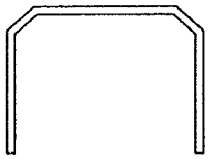
FIG. 2D, shows a cross section of a rectangular shape with straight sides followed by a bevel, angled line, or curved shape near a top surface.
Figure 2E:
FIG. 2E shows a cross section of a rounded shape (including e.g. a half circle)
Figure 2F:
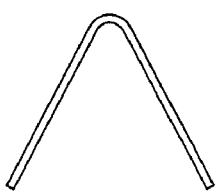
FIG. 2F, shows a cross section of a triangular shape with a either a relatively sharp top edge, slanted top edge, or a rounded top edge.

Ribs 101 are now discussed in more detail. Many shapes are thought to be suitable for creating ribs 101 on a shroud 102. FIGS. 2A-2F depict some exemplary suitable shapes. FIG. 2A shows a cross section of a rectangular rib; FIG. 2B, a rectangular shape with rounded sides; FIG. 2C a rectangular shape with slanted or angled sides; FIG. 2D, a rectangular shape with straight sides followed by a bevel, angled line, or curved shape just before a top surface; FIG. 2E a rounded shape (including e.g. a half circle); FIG. 2F, a triangular shape with a either a relatively sharp top edge, slanted top edge, or a rounded top edge.

The height of a rib 101 should be about 0.002 inches or more as measured from near an outer surface of shroud 102 to the top edge or surface of the rib, such as where the rib can come into contact with a disposable cover, typically a slide-on disposable cover.

The width of a rib 101 near the outer surface of shroud 102 should be sufficient to provide reliable mechanical contact with the outer surface of shroud 102. Minimizing the width of a rib 101 near the outer surface of shroud 102 can be helpful to increase the thermal resistance of the conductive heat flow path from a disposable cover to the IR tip assembly 100. Minimizing the width of a rib 101 near the outer surface of shroud 102 also can help to create larger volumes of insulating air present in the volume bounded by the outer surface of shroud 102, the ribs, and the inner surface of a disposable cover.

In some embodiments, a linear rib pattern can provide a suitable pattern for ribs 101 disposed on a shroud 102 of an IR tip assembly 100. In a linear rib pattern, ribs 101 substantially follow a guide line 106 from near the proximal end of shroud 102 (near the IR thermometer body) to a near a distal end of shroud 102 (farthest from the IR thermometer body). For the linear rib pattern, generally three ribs can hold a disposable cover at roughly a similar height above the outer surface of shroud 102. More ribs can be used, such as the eight rib embodiment shown in FIG. 1C and FIG. 1D. As the number of ribs in a linear rib pattern increase, the tradeoff is lowered air volume and increased conductivity between the disposable cover and the tip (lower net thermal resistance).

FIG. 3A and FIG. 3B show respectively a perspective and a side view of another suitable pattern for ribs 101. In FIG. 3A and FIG. 3B, an IR tip assembly 100 includes a rib situated substantially orthogonal to the axis of guide line 105 in substantially circular patterns. Two or more ribs disposed in circular patterns can be used to hold a disposable cover at roughly a similar height above the outer surface of shroud 102. Or, there can be one circular rib and a mechanical connection of the disposable cover at the base of the disposable cover (not shown in FIG. 3A and FIG. 3B).

In yet another "witches hat" embodiment (e.g. FIG. 1B), the disposable cover attaching structure (an attaching feature) can cause there to be a mechanical connection between the disposable cover and the tip assembly at a base flange of the disposable cover. Where a releasable connection at the base of the disposable cover is used, there can be embodiments of the tip assembly having no ribs or nubs on an outer surface of the shroud above the base portion. FIG. 3C shows one embodiment of a tip assembly where a disposable cover (not shown) can releasably attach near a base of the tip assembly. In one such embodiment a base of a disposable cover can be releasably attached to a corresponding protuberance, such as a circular protuberance 121, on a shroud of a tip assembly. Note that a circular protuberance 121 can include one or more breaks between circular protuberance sections and need not be a continuous ring. Such breaks can be used to facilitate airflow under the cover. Also, any suitable protuberance or nubs or segments of protuberances can be used to releasably accept a disposable cover base (near the "rim" of the witch's hat). For example, in some embodiments seating features 104, FIG. 1C, can in some cases be sufficient alone to support an attached disposable cover with no additional feature, such as circular protuberance 121, needed.

Figure 4A:
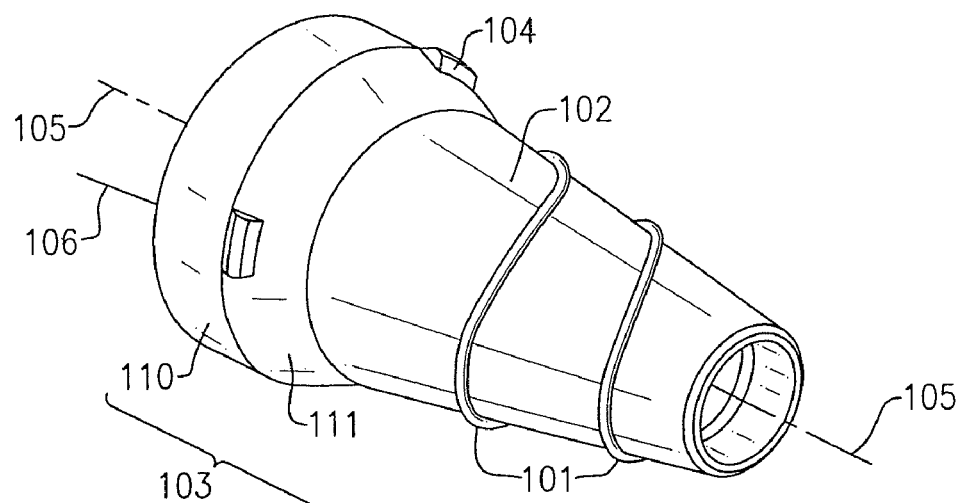
FIG. 4A shows a perspective view of an exemplary embodiment of a thermally isolating IR tip assembly having spiral ribs.
Figure 4B:
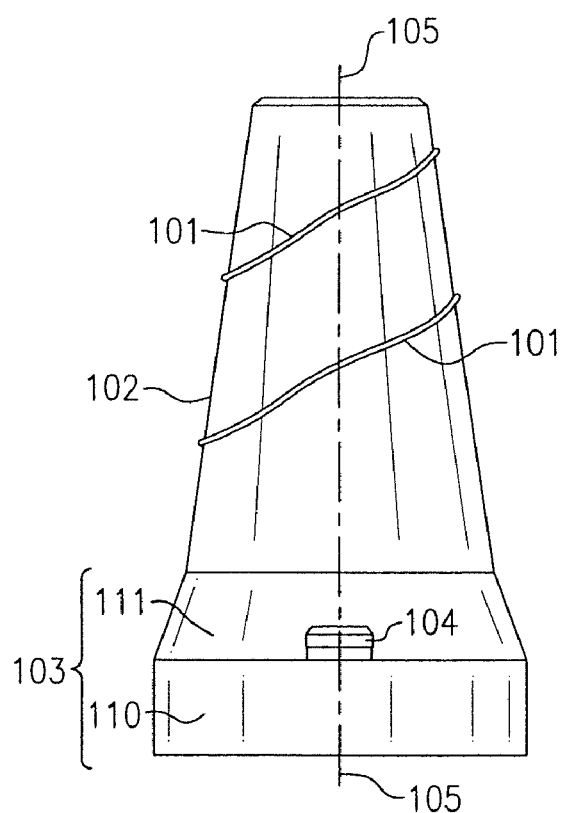
FIG. 4B shows a side view of the exemplary tip of FIG. 4A.

FIG. 4A and FIG. 4B show respectively a perspective and a side view of still another suitable pattern for ribs 101. In FIG. 4A and FIG. 4B, an IR tip assembly 100 includes a spiral or helical pattern (e.g. a screw thread like pattern). A spiral pattern can have a pitch ranging from large to small (analogous to the pitch of the thread of a machine screw). Advantages of a large pitch include a larger volume of air and lower thermal conductivity (higher thermal resistance. One advantage of a smaller pitch is greater friction to better affix a disposable cover to an IR tip assembly 100. Since a spiral or helical pattern rounds the outer surface of shroud 102 from near the proximal end of shroud 102 near the IR thermometer body) to a near a distal end of shroud 102, one such pattern can be sufficient to properly affix a disposable cover to an IR tip assembly 100. The pitch of a spiral or helical pattern need not be fixed and can vary in any way from the distal end to the proximal end of an IR tip assembly 100.

Also, regarding all three rib patterns as described above, the linear rib pattern, the circular pattern, the spiral or helical pattern, and any other suitable rib pattern that provides one or more volumes of insulating air while providing mechanical support for a disposable cover, such patterns need not be continuous. For example there can be breaks in the rib pattern of a linear rib (e.g. a dashed or dashed-dot linear broken rib pattern). Also, in a broken rib pattern, such as a dashed linear rib, the dashed section need not line up linearly from near the proximal end of shroud 102 (near the IR thermometer body) to a near a distal end of shroud 102. In fact, a similar pattern thought suitable can have a staggered linear sections of rib on the outer surface of shroud 102 in segments placed in directions other than linear directions from proximal end to distal end, including continuous spiral or circular patterns. For example, suitable rib 101 segments might be disposed in such angles that if drawn out as continuous ribs, would create overlapping helixes. Such rib segments can have any of the aforementioned shapes described for ribs 101.

Also, regarding all three rib patterns described above, the linear rib pattern, the circular pattern, the spiral or helical pattern, either with substantially continuous ribs or rib segments, each rib can be substantially linear or can include non straight sections, such as a zigzagged, squiggled, or similar curved section. In a limit of shortened segments, a plurality of contact points (e.g. protuberances such as bulges or knobs) can extend outwards from the outer surface of shroud 102 to support a disposable cover above the outer surface of shroud 102 and to provide the desired insulating volumes of air and minimal paths of thermal conductivity between the disposable cover and IR tip assembly 100. Such protuberances can have any of the aforementioned shapes described for ribs 101.

Figure 5:
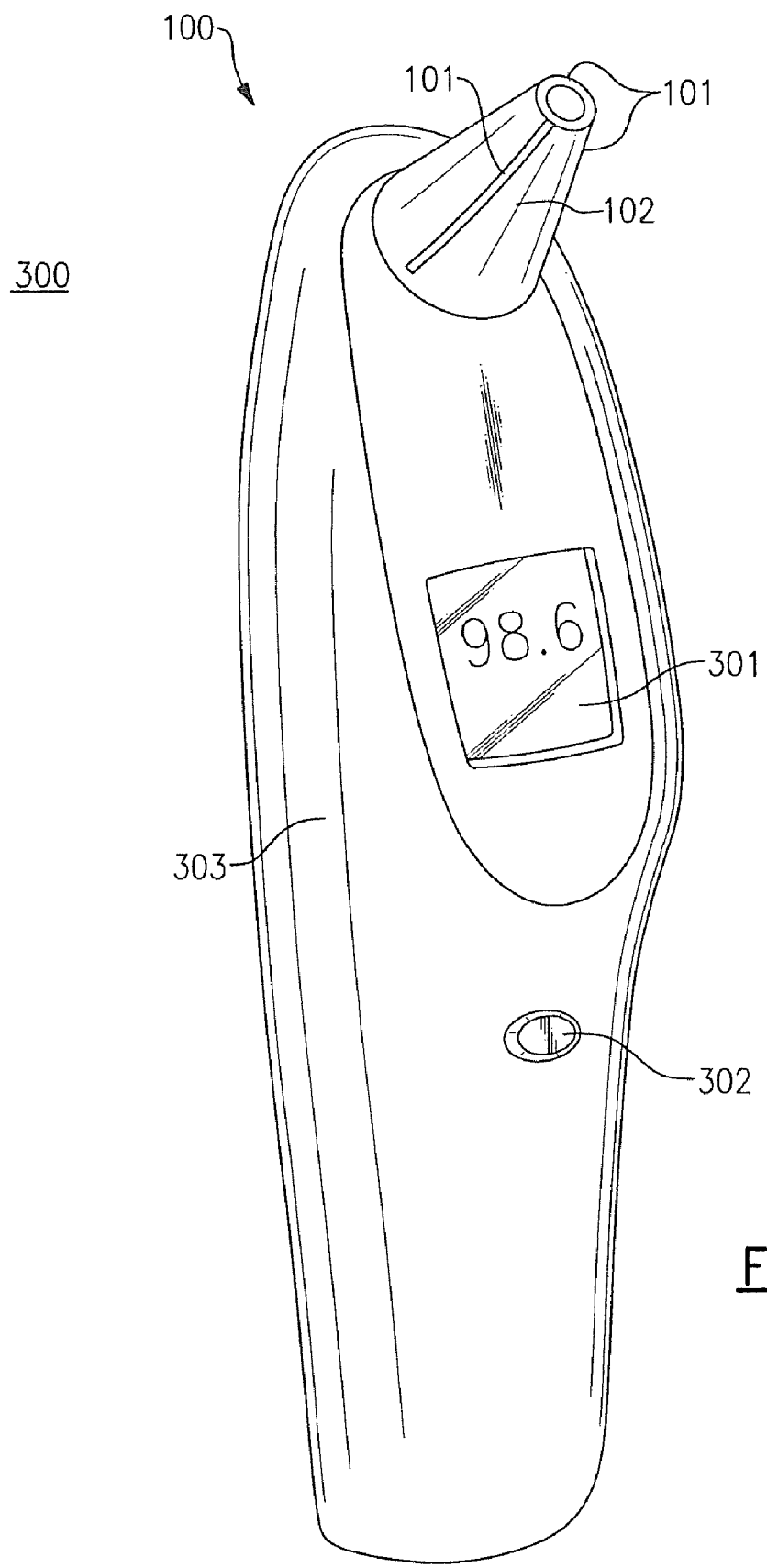
FIG. 5 shows an illustration of an exemplary IR ear thermometer having a tip with ribs.
Figure 5:
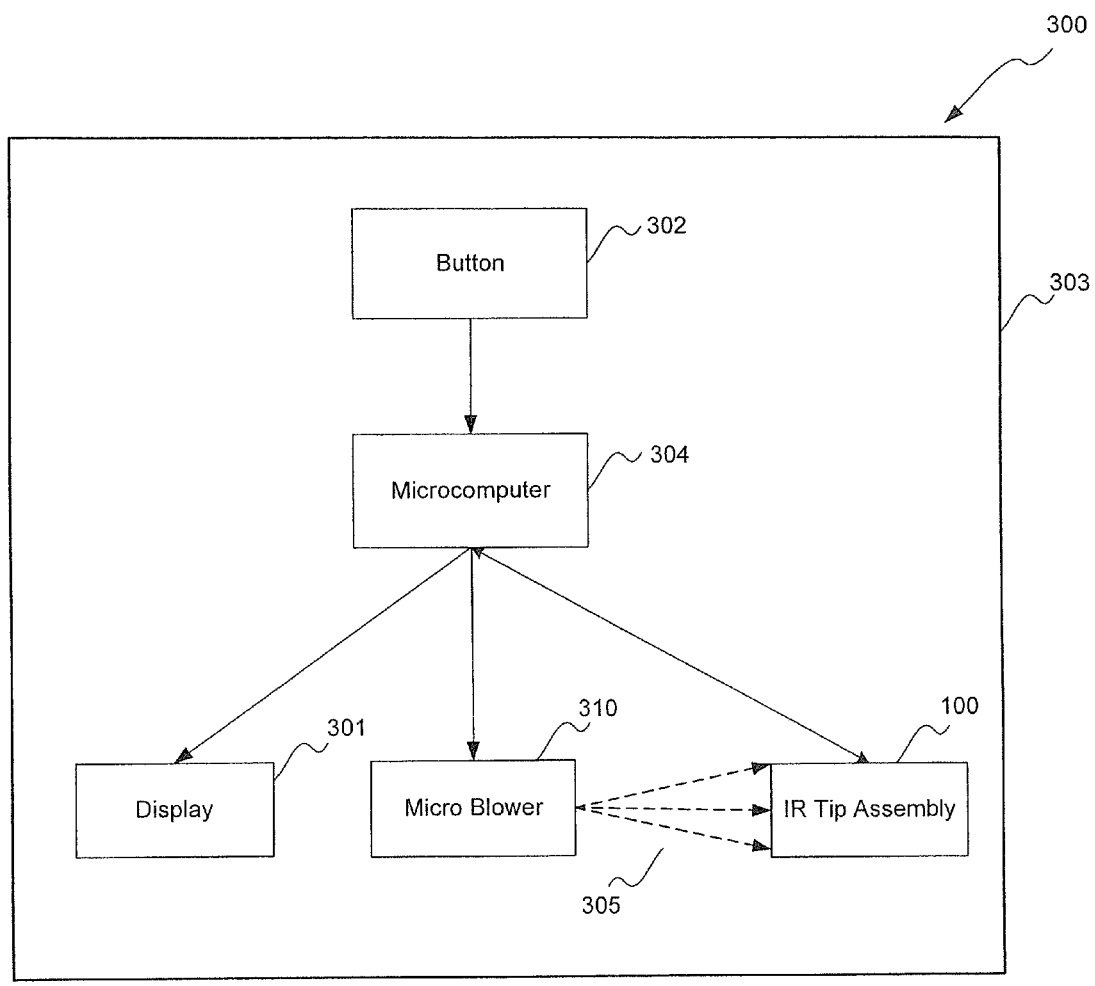
Figure 5:
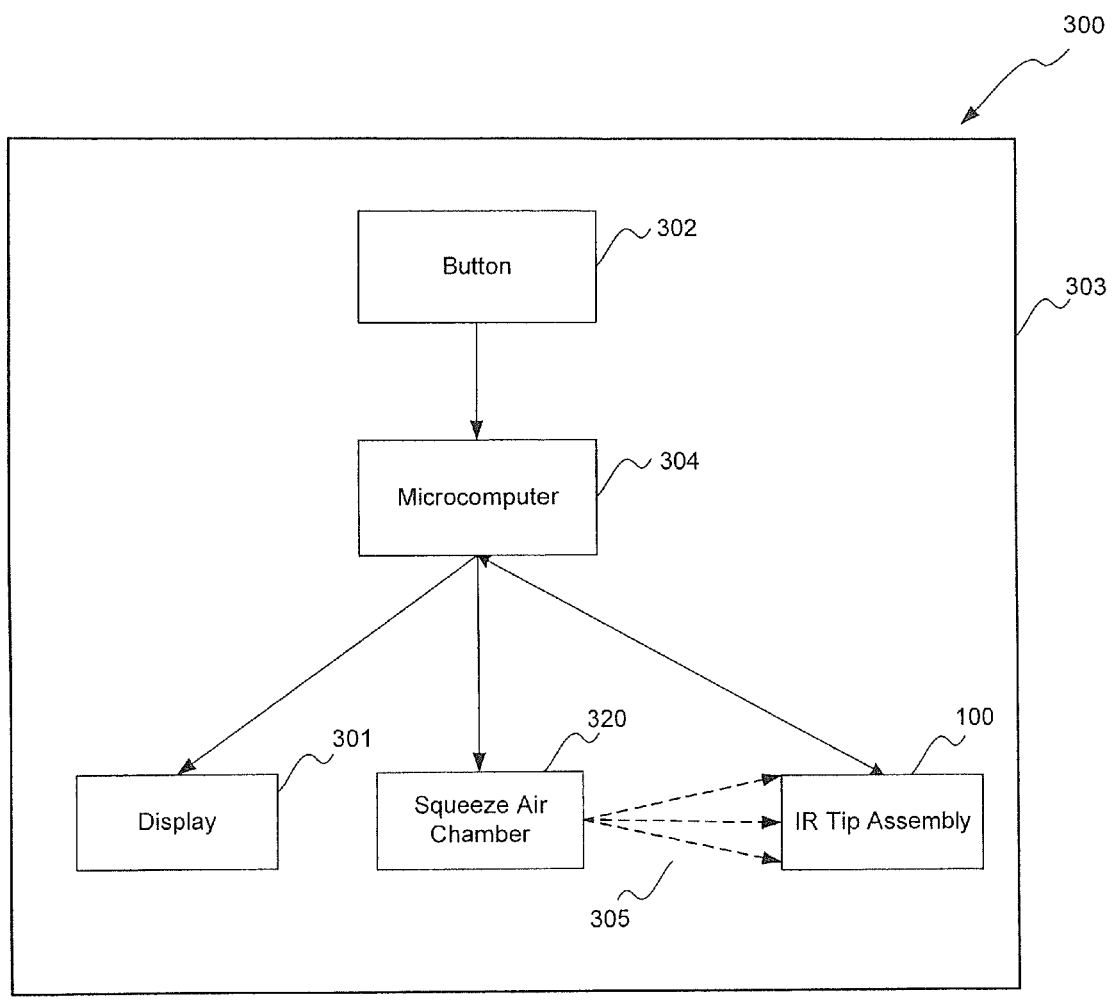
Figure 5:
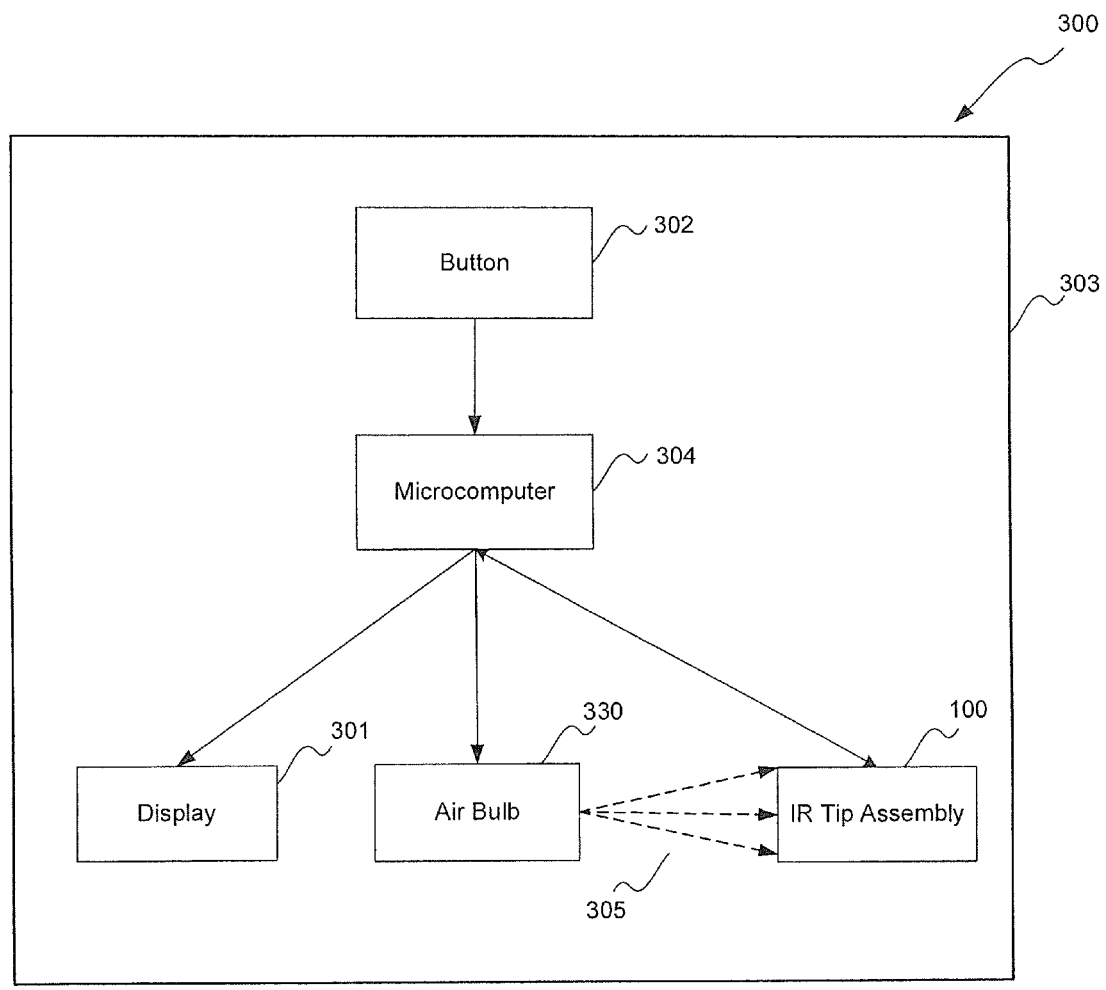
Figure 5:
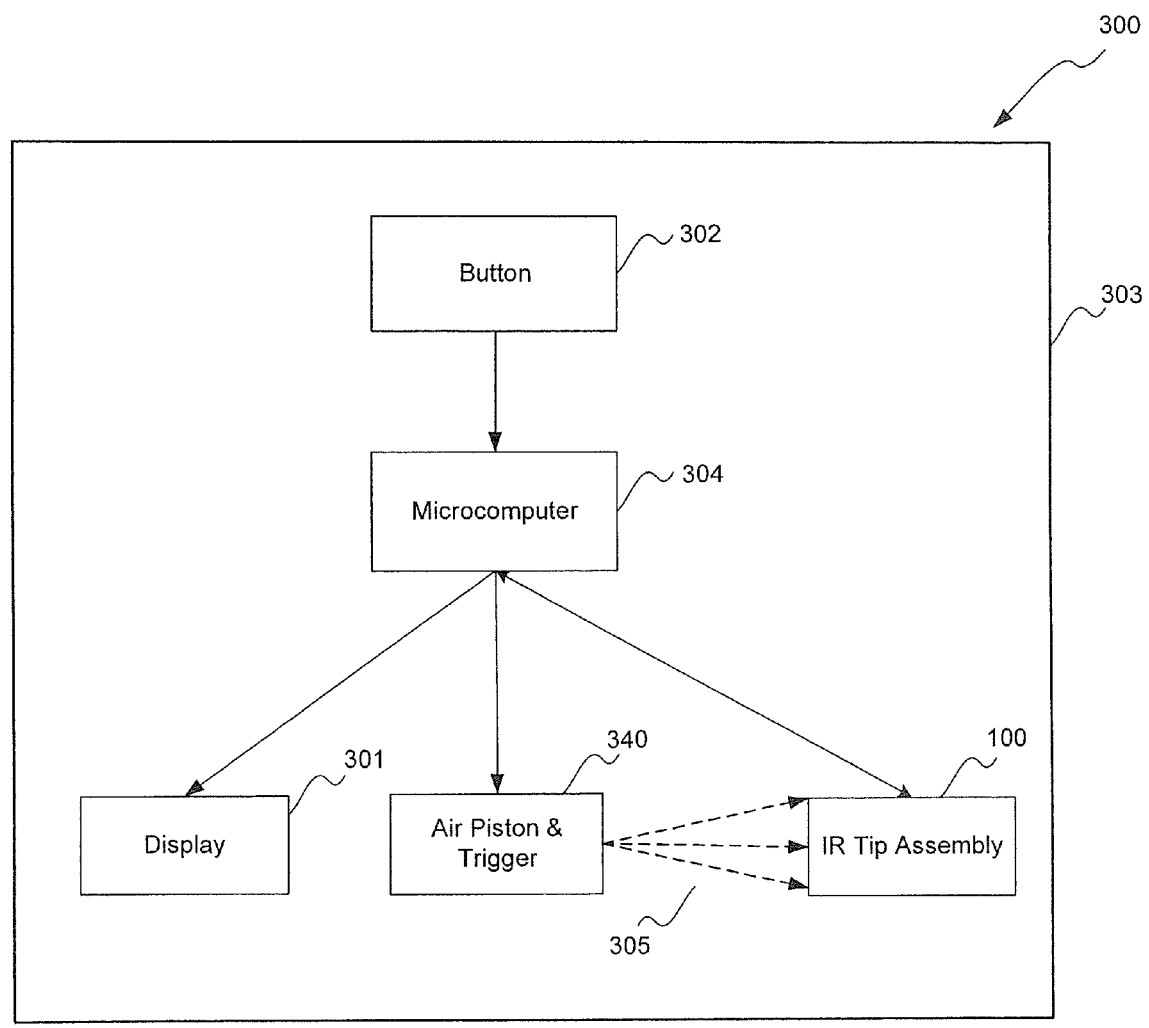

FIG. 5 shows an illustration of one exemplary embodiment of an IR ear thermometer 300 having an IR tip assembly 100 with ribs 101. Here three ribs are shown in a linear rib pattern. In this exemplary embodiment, ribs 101 substantially follow the outer surface of shroud 102 from near the proximal end of shroud 102 near the IR thermometer body to a near distal end of shroud 102. Also in this embodiment, there is no discernable separate base section 103 since the shroud 102 begins substantially at the IR thermometer body 303. IR thermometer body 303 also houses suitable electronics including a microcomputer 304 (shown in FIGS. 5A-D) running a program that is configured to compute a temperature of a patient based an electrical signal from an IR sensor. In some embodiments, a button 302 can be depressed to take a reading that can then be displayed on a display 301. It is unimportant where mode and measure buttons and a display are physically located on IR thermometer body 303.

Turning now to the IR sensor, typically a thermal sensor, such as a thermopile sensor, receives IR radiation, such as in the case of an IR ear thermometer, from a patient's tympanic membrane. One exemplary thermopile sensor suitable for such use is the TPS 23B/3367 thermopile sensor available from PerkinElmer of Salem, Mass.

Figure 6:
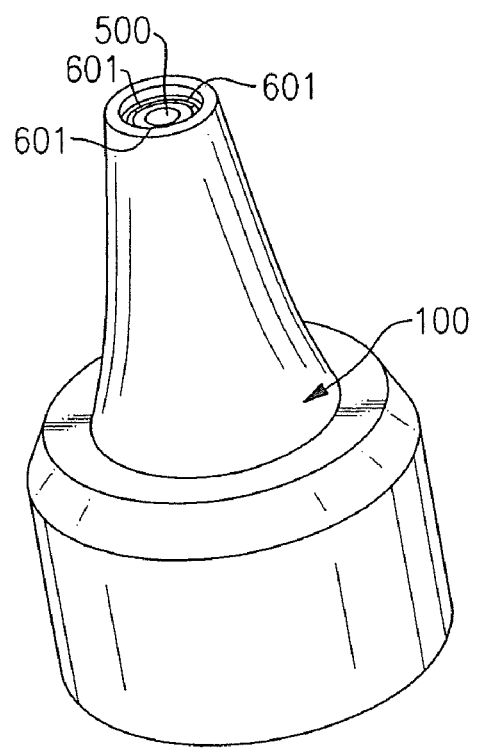
FIG. 6 shows a perspective view of an IR tip assembly having a thermally isolated IR sensor.
Figure 7:
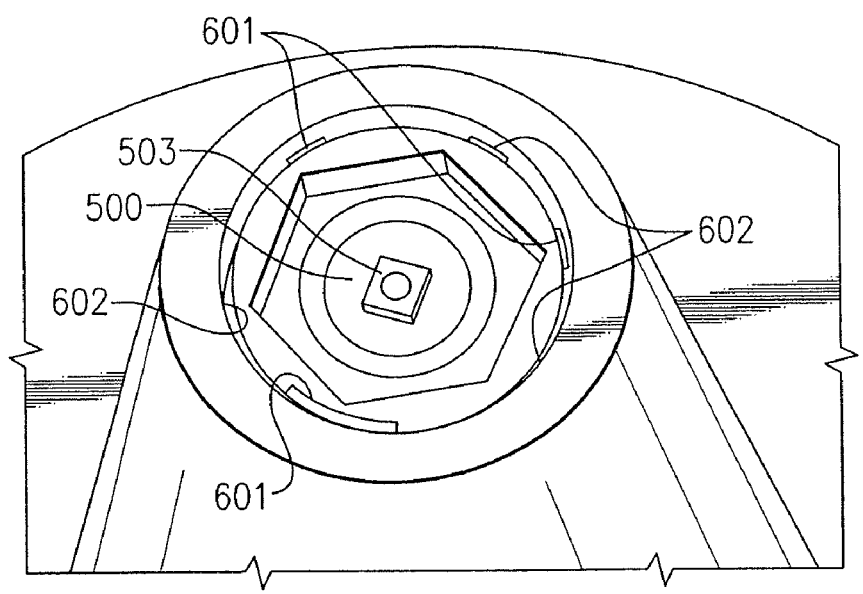
FIG. 7 shows a more detailed end view of the IR tip assembly of FIG. 6.

Turning now to FIG. 6, one exemplary technique of thermal sensor thermal isolation is now described. FIG. 6 shows a perspective view of an IR tip assembly having a thermally isolated IR sensor. Thermal sensor 500 is thermally isolated from IR tip assembly 100 by sensor supports 601. In the exemplary embodiment of FIG. 6, three supports are shown, the exact number of supports is unimportant and more than three supports can be used. FIG. 7 shows a more detailed end view of the IR tip assembly of FIG. 6. FIG. 7 shows that there are voids or volumes of air created between the inner surface of the tip, the outer surface of the sensor package (e.g. an isothermal housing 503), and the sides of the sensor supports. The sensor air gaps or air pockets 602 created by the voids are thermally insulating features that further limit the flow of heat energy from IR tip assembly 100 into the thermal sensor package. In still other embodiments as discussed hereinbelow, an IR sensor 500 can be mounted on a free standing support, such as a part of a heat sink and separated from a tip section of an IR tip assembly by an air gap (e.g. an air gap between the side of an IR sensor and the shroud), thus no longer needing the thermally insulating supports described above.

IR tip assemblies having heat sinks are now described in more detail. Several embodiments of IR tip assemblies that use tip ribs (ribs 101, FIG. 1) or other suitable structures to thermally isolate an IR thermometer heat sink tip from a disposable cover are now described. In the prior art, IR thermometers have had internal heat sinks. Those internal heat sinks have typically been surrounded by thermally insulative materials. The goal of the heat sink is to accept heat energy, especially including undesired heat flow, such as typically flows into the IR thermometer from the outside environment, and to keep that heat energy from significantly changing the temperature of the IR sensor case and materials surrounding the IR sensor case. Since heat sinks are made from relatively high capacity materials, for a given inflow of heat energy, there is a relatively small corresponding increase in heat sink temperature as compared to a temperature change that would occur without the heat sink. However, there is still an increase (or decrease) in temperature, albeit smaller with a heat sink present. Conventional prior art designs typically surrounded IR thermometer heat sinks with thermally insulative structure and materials to reduce heat flow between the heat sink and the environment.

Figure 8:
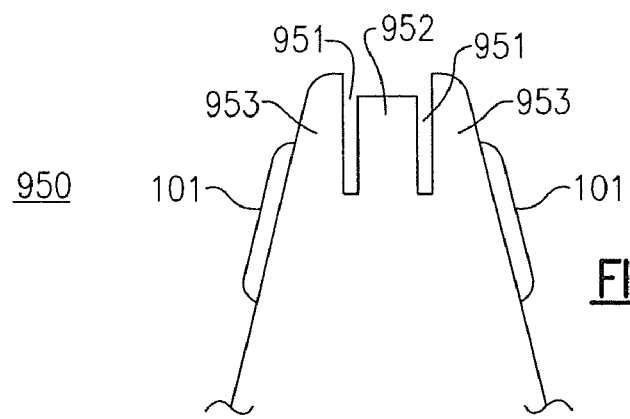
FIG. 8 shows a sketch of one exemplary embodiment of a heat sink tip having ribs.

FIG. 8 shows a sketch of one exemplary embodiment of a heat sink tip 950 having ribs 101. In the embodiment of FIG. 8, in addition to the thermal insulation provided by air gaps created in the spaces between ribs 101 under a disposable cover (not shown in FIG. 8) there is another air gap 951 provided between IR sensor 500 (IR sensor not shown, the IR sensor is mounted to heat sink section 952) and heat sink sections 953. Note that in some embodiments, air gap 951 eliminates the need for thermally isolating materials such as sensor supports 601, FIG. 6 as described above.

Figure 9:
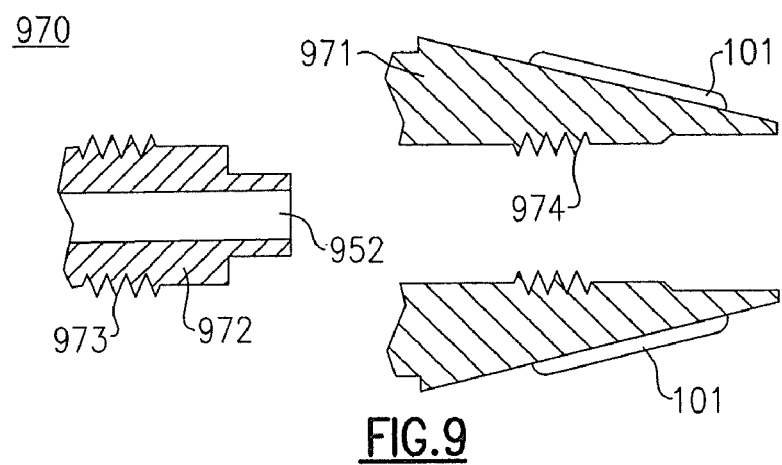
FIG. 9 shows a sketch of a heat sink tip made from two pieces that can be used to create a single assembled single heat sink tip.

A heat sink tip 950 can be fabricated from any suitable heat sink material, such as, for example, any suitable metal. Suitable metals include, for example, steel, brass, copper, copper alloys, aluminum, and aluminum alloys. Heat sink tips 950 can be fabricated by known techniques, such as by molding or injection molding. An IR sensor 500, FIG. 5, can be mechanically and thermally attached to a mounting section 952 of a heat sink tip 950. Heat sink tips 950 can be fabricated in a single piece of material, typically a metal, or in two or more pieces of material that can then be assembled into a heat sink tip. For example, FIG. 9 shows a sketch of a heat sink tip made from two pieces that can be used to create a single assembled single heat sink tip. In the exemplary embodiment of FIG. 9, heat sink tip 970 is made from two pieces, a core section 972 having threads 973 that can be screwed into threads 974 of an outer section 971 to create a single heat sink tip. As in the embodiment described above, an IR sensor 500 can be mechanically and thermally attached to a mounting section 952 of heat sink tip 970. Note that while heat sink tip 950, FIG. 8 and heat sink tip 970, FIG. 9 both show exemplary ribs 101, any suitable structures as described above can be used to create an air gap between the heat sink tip and a disposable cover.

Since the new tip ribs provide surprisingly significant thermal isolating properties, it is also now possible to make the shroud structure substantially from heat sink material. Therefore, in some embodiments, there is no longer a need for an outer plastic thermally insulating shroud and the shroud can be made from a thermally conductive material. In such cases, the shroud effectively becomes part of the heat sink. In yet other similar embodiments, there can still be an additional thermally insulating layer disposed between the shroud and the disposable cover. For example, in some embodiments, instead of ribs 101 mounted directly to a surface of heat sink sections 953 as discussed above, there can be an additional thermal isolation layer, such as an additional insulating layer over the shroud (not shown in FIG. 8 and FIG. 9). A thermally insulating layer can be made from any suitable material, such as a plastic, and mechanically attached, for example by threads, to a tip section. For example, a heat sink section 953, FIG. 8, or a heat sink section 971, FIG. 9 can have additional threads (not shown) on an outer surface so that an insulative layer (not shown) can be screwed on to the shroud section to attach an additional insulative layer over the shroud of the heat sink. In such cases, supporting features, e.g. ribs 101, to support a disposable cover can be present on the outer surface of the insulative layer instead of on the outer surface of the shroud. In embodiments having an additional insulating layer, one or more insulating air gaps can be created between an outer surface of the additional insulative layer and the disposable cover. Where an additional layer of insulative material overlays the shroud a cover attachment feature and/or other protuberances such as nubs or ribs can be disposed at least in part on an outer surface of the additional layer of insulative material. The cover attachment feature and/or other protuberances such as nubs or ribs can create one or more air gaps between the outer surface of the additional layer of insulative material and the inside surface of the disposable cover. Such an insulating layer can make thermal contact with the shroud primarily at the attaching threads, thus "wicking" any absorbed heat to the heat sink.

Figure 10:
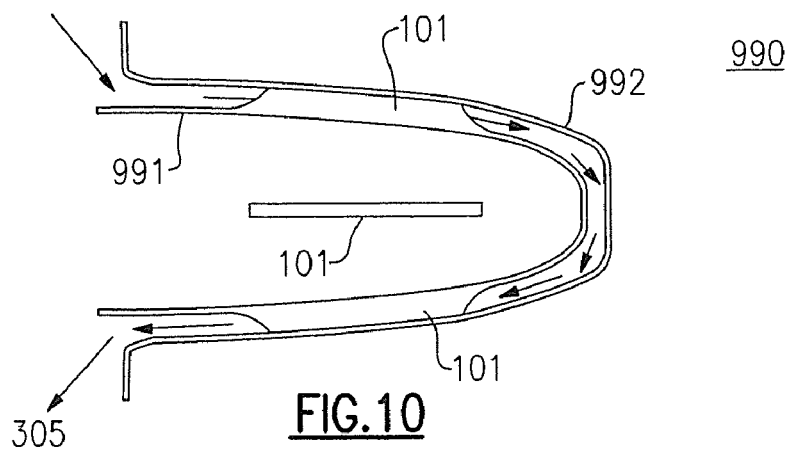
FIG. 10 shows a partially broken away view of one exemplary embodiment of a tip having an airflow through air gaps between its ribs.

Turning now to tips that have airflow in an air gap between a tip section and a disposable cover, FIG. 10 shows a cutaway side view of another embodiment of a tip 990 having ribs 101. The tip of FIG. 10 has airflow 305 through air gaps between its ribs 101. In any of the embodiments described hereinabove, the tip and ribs 101 can be configured such that when a cover 992 is affixed to a tip, such as tip 991 of FIG. 10, there can be an airflow as indicated by the arrows of FIG. 10. The exact direction if the airflow is unimportant. Such an airflow can be a convective airflow as caused by thermal gradients, such as, for example, caused by thermal gradients present between the tip and the auditory canal of a patient present when an IR ear thermometer is inserted into the ear of patient. It is believed that such convective currents flowing beneath a cover 992 and between ribs 101 of a tip provide useful thermal insulating properties. For example, in most embodiments, a tip 991 and tip ribs 101 have a higher heat capacity than a disposable cover 992. In the case of heat sink tips 950, where the tip 991 and tip ribs 101 are typically made from a metal, the heat capacity of the tip and ribs is much larger than the heat capacity of the cover 992, typically made from a plastic. Therefore, an airflow as shown by the arrows of FIG. 10 tends to hold the temperature of the tip and tip ribs, further preventing a rise (or fall) in tip temperature caused by undesirable heat flow from a cover 992.

Turning now to embodiments of a thermally isolating tip assembly having forced airflow, various techniques for causing the forced airflow 305 between a disposable cover and the shroud are now described. In one embodiment, a forced airflow can be caused by a micro blower 310, such as a micro fan blower, as shown in FIG. 5A. The blower can be disposed either in the tip assembly or in an attached IR thermometer body. In another embodiment, a squeeze IR thermometer handle 320, as shown in FIG. 5B, (with air chambers) blows air through the air gap under the disposable cover (e.g. positive airflow on squeeze, and negative airflow on relaxation). In another embodiment, an air bulb 330, as shown in FIG. 5C, can be manually squeezed to cause airflow under the disposable cover. And, in yet another forced air embodiment, when the IR temperature measure trigger is pulled, an air piston 340, as shown in FIG. 5D, (e.g. a pneumatic piston) can be simultaneously moved by the trigger movement to cause airflow through the gap between the disposable cover and the shroud.

Yet another reason to limit heat flow between the auditory canal and an IR tip assembly is that the undesired heatflow ("draw down") can cause changes of the temperature of the auditory canal (by conductive heat flow enhanced by blood flow) and can also change the temperature of the tympanic membrane (which induces an error in the temperature measurement). Such errors become worse when a practitioner takes multiple successive readings. Thus, there are other reasons to limit tip assembly heat flow from the outside environment, beyond the desire to minimize a temperature change of the IR sensor as previously described.

We turn now to the process and protection of heat flow throughout the duration of the measurement. When an IR thermometer is, for example, inserted into the auditory canal of a patient to make a temperature measurement, initially, the first interface air gap between the disposable cover and the shroud is sufficient, however, eventually undesired heat, such as by conduction from the wall of the auditory canal, penetrates this interface. The second line of defense against undesired heat flow into the tip assembly is the shroud/heat sink interface that can wick heat to the heat sink after it has passed through the first air gap. Then the second air gap interface between the shroud and the side of the IR sensor provides another line of defense to further protect the sensor as the measurement completes.

We now briefly discuss thermal modeling which has confirmed the sequence of heat flow as described above. Studies were made of various IR tip assembly configurations. In general it was found that while initially, radial heat flow dominates in an IR tip assembly, after about 2.5 seconds, axial heat flow begins to take over. Through thermal modeling, the later axial heat flow was found to be the most prominent change of IR sensor temperature change with time, a potential source of IR temperature measurement error. As described hereinabove, an air gap between a disposable cover and an IR tip assembly, such as can be provided by tip ribs, can significantly reduce undesirable heat flow between the cover and the IR tip assembly. Also, as described above, undesired heat flow can be further minimized by use of air gaps at the sensor package (e.g. air gaps surrounding the sides of an IR sensor 500) and by use of a heat sink thermally coupled to the base of the IR sensor.

Turning now to an example of one thermal model, FIG. 11A shows an exemplary cut away line drawing of an axi-symmetric thermal model of one half IR tip assembly 1201 with an attached disposable cover 1202. FIG. 11B shows an exploded view of the IR tip assembly of FIG. 11A. Disposable cover 1202 is thermally isolated from the shroud 102 by an air gap 1203. In the thermal model, air gap 1203 represents a cover supported by ribs. A heat sink 1204 is shown thermally coupled to an IR sensor 500 having an IR sensor window 502. The heat sink 1204 is thermally isolated by a heat sink air gap 1205.

Figure 12:
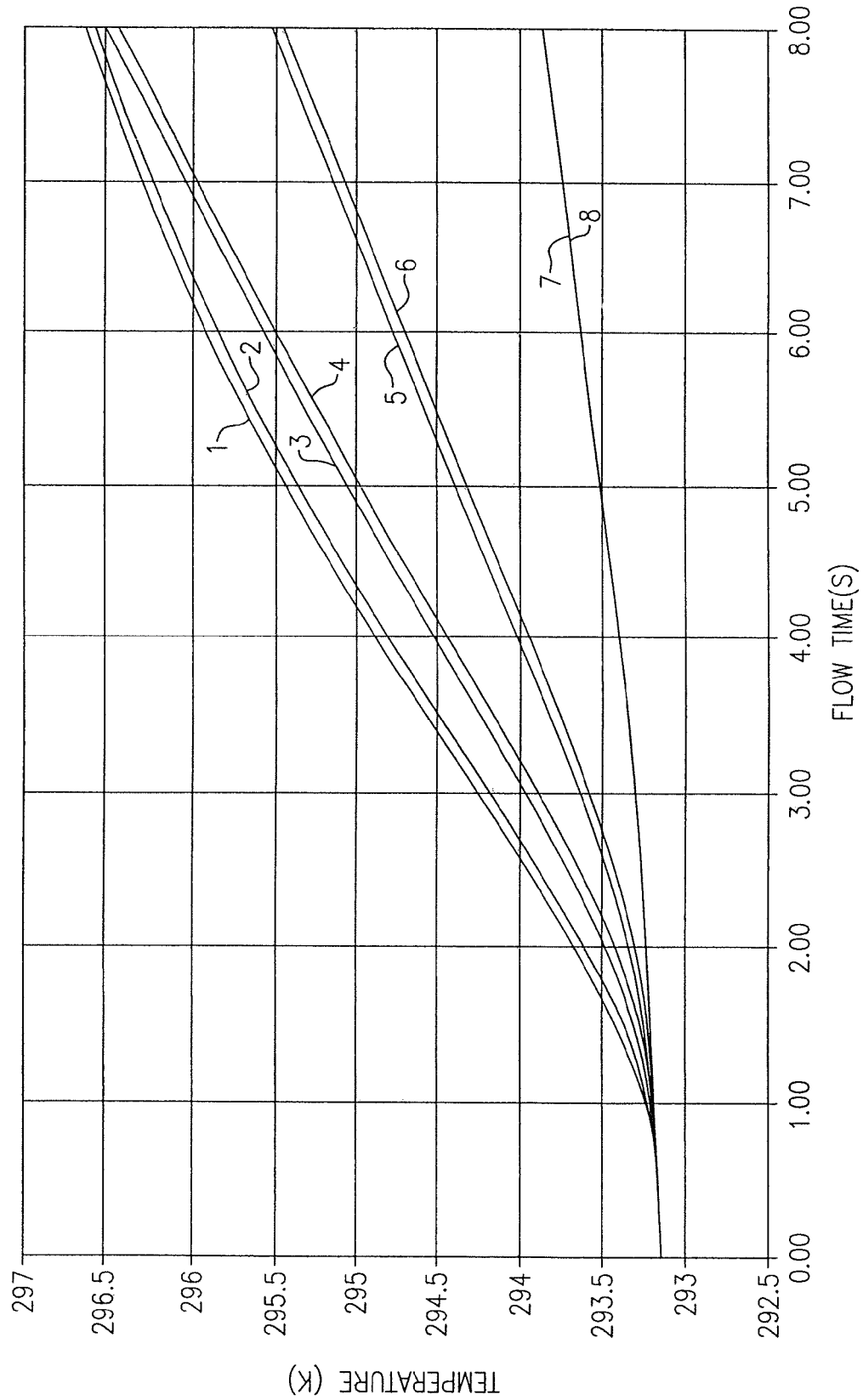
FIG. 12 shows a graph of thermally modeled transient temperature changes versus time.

FIG. 12 shows a chart of thermally modeled transient temperature changes. The graph shows four pairs of curves (labeled 1 2-3 4-5 6-7 8) of temperature plotted against flow time, i.e. the duration of the transient event. For each pair of curves, the upper curve shows the temperature at the base of the sensor in the heat sink area, and the lower curve shows the temperature at the thermistor chip inside the sensor. The four curves show how undesired temperature changes at the IR sensor can be minimized during an IR thermometer temperature measurement by use of the gap between the disposable cover the shroud. Note that the flatter curves showing the least amount of change in temperature at the IR sensor are most desirable. Four scenarios were modeled. Curves 1 and 2 show the largest changes in temperature with no disposable cover where the shroud is exposed. Curves 3 and 4 show the temperature changes for a disposable cover present, but without a significant air gap between the disposable cover and the shroud. The first significant reduction of change in temperature during a modeled measurement was found to begin at about an air gap of 0.002" between the disposable cover and the shroud as shown by curves 5 and 6. Still more improvement was achieved with an air gap of 0.02" as shown by the flattest curves, 7 and 8.

It was concluded from tests results, such as those described above using the exemplary graph of FIG. 12 that a disposable cover thermally isolated by ribs can help to minimize problematic IR sensor temperature changes during IR temperature measurements. Surprisingly, it was found that the beneficial nature of such ribs continues down to about rib dimensional heights as small as 0.002" above the surface of a shroud 102 or a tip shroud overlaying a shroud 102. It was also realized through theoretical thermal modeling and lab experiments that additional air gaps between the inside surface of an IR tip assembly and an IR sensor can or package can further minimize undesired changes in the sensor chip temperature during a typical clinical IR temperature measurement. Finally, further reduction of undesired change of temperature of the IR sensor and reduction of undesired thermal gradients near the IR sensor can be attained by a heat sink well bonded (making good thermal contact) with the IR sensor can or package.

Many functions of computer based apparatus, such as the IR thermometers described herein, can be implemented in hardware (for example, hard-wired logic or other integrated circuitry), in software (for example, using instructions encoded in a program operating on a general purpose processor or on a specially designed processor), and in firmware (for example, using instructions encoded in a non-volatile memory that is accessed for operation on a processor as required) or some combination thereof. The present invention contemplates the substitution of one implementation of hardware, firmware and/or software for another implementation of the equivalent functionality using a different one of hardware, firmware and/or software. To the extent that an implementation can be represented mathematically by a mathematical function, that is, a specified response is generated at one or more output terminals for a specific input or inputs applied to one or more input terminals of a "black box" exhibiting the mathematical function, any implementation of the mathematical function, including any combination of hardware, firmware and/or software implementations of portions or segments of the mathematical function, is contemplated herein.

"Microcomputer" is defined herein as synonymous with microprocessor, microcontroller, and digital signal processor ("DSP"). It is understood that memory used by the microcomputer, including for example an algorithm to perform an IR thermometer operation can be coded as "firmware" that can reside in memory physically inside of a microcomputer chip or in memory external to the microcomputer or in a combination of internal and external memory. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

While the present invention has been particularly shown and described with reference to the preferred mode as illustrated in the drawing, it will be understood by one skilled in the art that various changes in detail may be affected therein without departing from the spirit and scope of the invention as defined by the claims.

We claim:

1. A thermometer having an IR tip assembly, the IR tip assembly comprising:
   an IR sensor disposed within said IR tip assembly;
   a heat sink coupled to said IR sensor base;
   a shroud overlying said IR sensor and said heat sink, said shroud including at least one cover attachment feature; and
   an airflow feature configured to provide an airflow at least partially over an outer surface of the shroud.

2. The thermometer of claim 1, wherein a base of said shroud includes an annular protruding section, said protruding section being adapted to releasably accept a base of a cover.

3. The thermometer of claim 2, including a gap of at least 0.002" between a portion of an inner surface of said cover and the outer surface of said shroud when said cover is attached.

4. The thermometer of claim 1, wherein said shroud includes at least one raised contact element on an exterior of said shroud.

5. The thermometer of claim 4, wherein said at least one raised contact element comprises a nub.

6. The thermometer of claim 4, wherein said at least one raised contact element comprises at least one rib.

7. The thermometer of claim 6, wherein said at least one rib comprises at least a selected one of a linear rib, a spiral rib, and a circular rib.

8. The thermometer of claim 6, wherein a plurality of ribs are disposed on said exterior of said shroud in a substantially linear pattern, each rib running from a proximal end to a distal end of said shroud.

9. The thermometer of claim 6, wherein a plurality of ribs are disposed on said exterior of said shroud in a substantially linear pattern, each rib having a length dimension that is less than the length from said proximal end to said distal end.

10. The thermometer of claim 6, including a plurality of rib segments distributed along said exterior of said shroud.

11. The thermometer of claim 1, wherein said shroud is a part of said heat sink.

12. The thermometer of claim 11, wherein said heat sink comprises a metal selected from the group consisting of steel, brass, copper, copper alloy, aluminum, and aluminum alloy.

13. The thermometer of claim 1, wherein said tip assembly further comprises at least one air gap between an IR sensor side surface of said IR sensor and said shroud.

14. The thermometer of claim 13, wherein said tip assembly further comprises a plurality of insulative members between said IR sensor side surface and said shroud.

15. The thermometer of claim 1, wherein said tip assembly is threadedly attached to an IR thermometer body.

16. The thermometer of claim 15, wherein an additional layer of insulative material overlays said shroud.

17. The thermometer of claim 1 further comprising
   a microcomputer-based circuit electrically coupled to said IR sensor, said microcomputer-based circuit configured to accept an electrical signal from said IR sensor and to generate a mammalian body temperature based at least in part on said electrical signal from said IR sensor.

18. The thermometer of claim 1, wherein said airflow feature comprises a micro fan blower.

19. The thermometer of claim 1, wherein said airflow feature comprises an IR thermometer body having at least one squeezable air chamber.

20. The thermometer of claim 1, wherein said airflow feature comprises a pneumatically attached air bulb.

21. The thermometer of claim 1, wherein said airflow feature comprises an air piston mechanically coupled to a temperature measure trigger.

22. A method to enhance the thermal isolation of an IR thermometer IR sensor during a temperature measurement comprises the steps of:
   providing an IR thermometer having at least one air gap disposed between an IR sensor and a disposable cover; and
   causing airflow through said at least one air gap during a temperature measurement to reduce a temperature change of said IR sensor caused by undesired heat flow across said disposable cover.

23. The method of claim 22, where said step of causing airflow comprises causing airflow through said at least one air gap by squeezing an air chamber on an IR thermometer body.

24. The method of claim 22, where said step of causing airflow comprises causing airflow through said at least one air gap by squeezing an air bulb pneumatically coupled to said air gap.

25. The method of claim 22, where said step of causing airflow comprises causing airflow through said at least one air gap by air pressure from a micro blower.

26. The method of claim 22, where said step of causing airflow comprises causing airflow through said at least one air gap by air pressure from a pneumatic piston that moves when an IR temperature measurement trigger is pulled.

27. The thermometer of claim 1, wherein said airflow feature comprises a convective means.

28. A thermometer having an IR tip assembly, the IR tip assembly comprising:

an IR sensor disposed within the IR tip assembly;

a heat sink coupled to the IR sensor base;

a shroud overlying the IR sensor and the heat sink, said shroud including a cover attachment feature;

a cover attached to the shroud via the cover attachment feature; and an air gap disposed between an inner surface of the cover and an outer surface of the shroud; and an airflow feature configured to provide an airflow to the air gap.

29. The thermometer of claim 28, wherein said airflow feature comprises a fan.

30. The thermometer of claim 28, wherein said airflow is convective airflow.

* * * * *